United States Patent [19]

Whitehouse et al.

[11] Patent Number: 4,559,043
[45] Date of Patent: Dec. 17, 1985

[54] ASSEMBLY WITH SEPTUM FITTING FOR CONNECTING ADAPTOR AND FLUID TUBE

[75] Inventors: Craig M. Whitehouse; Daniel R. Snyder, both of Branford, Conn.; Ronald B. Luther, Newport Beach, Calif.

[73] Assignees: DRS Infusion Systems, Inc., New Haven, Conn.; Luther Medical Products, Inc., Santa Ana, Calif.

[21] Appl. No.: 665,572

[22] Filed: Oct. 29, 1984

[51] Int. Cl.[4] .............................................. A61M 5/00
[52] U.S. Cl. .................................... 604/201; 604/243; 604/283
[58] Field of Search .............................. 604/201–206, 604/240, 243, 283, 86, 88, 280

[56] References Cited

U.S. PATENT DOCUMENTS

| | | | |
|---|---|---|---|
| 3,158,155 | 11/1964 | Myerson | 604/202 |
| 3,739,779 | 6/1973 | Pfleger | 604/205 |
| 3,989,044 | 11/1976 | Meierhoefer | 604/243 |
| 4,187,848 | 2/1980 | Taylor | 604/243 |

Primary Examiner—John D. Yasko
Attorney, Agent, or Firm—Willie Krawitz

[57] ABSTRACT

An assembly for connecting needles and catheters in I.V. applications, chemical analysis, etc., includes a leak proof, sterile, self-sealing septum from which the needle is inserted. When the needle is retracted from the septum, the septum will reseal and thus maintain a leak-proof, sterile seal. The assembly is therefore reuseable, and this represents a considerable cost saving for patients who require continuous therapy such as with diabetics, cancer patients, and the like.

The assembly includes a distal end having an outlet bore through which a catheter is inserted. The proximal end of the assembly is connected to an external adaptor to which is attached a needle. The septum is positioned between the distal end and the proximal end to provide a self-sealing seal between the needle and the catheter. This external adaptor with needle may be part of a syringe or shaped to accommodate any standard connector such as a luer lock.

Depending on the application, the fittings may be manufactured from a wide range of materials including plastics and metal. For example, as an inexpensive disposable item, the fitting would preferably be manufactured from molded plastic.

19 Claims, 18 Drawing Figures

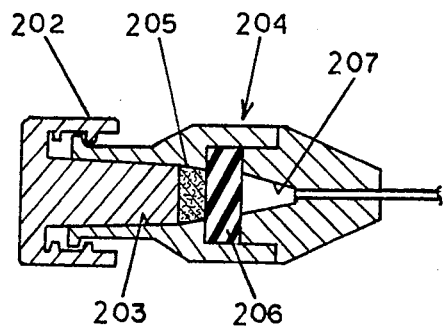
FIG. 14
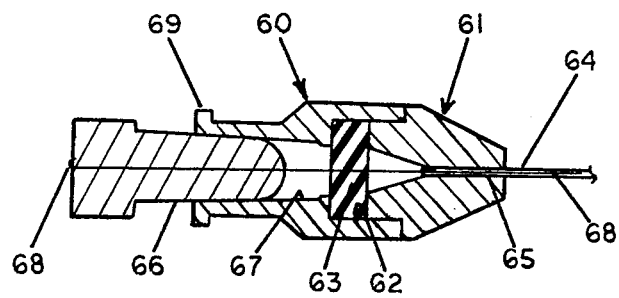
FIG. 5
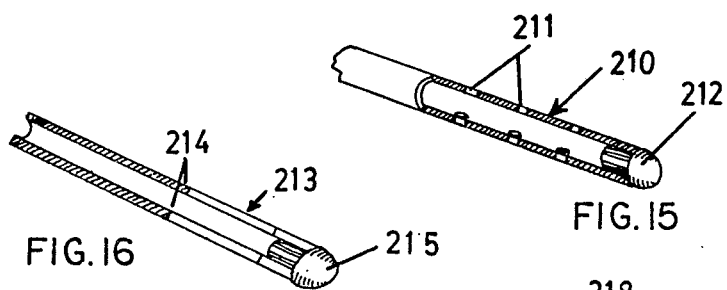
FIG. 15
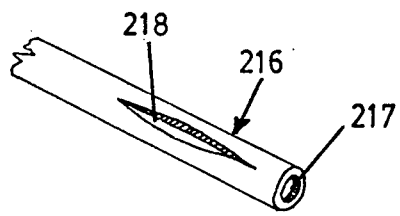
FIG. 17
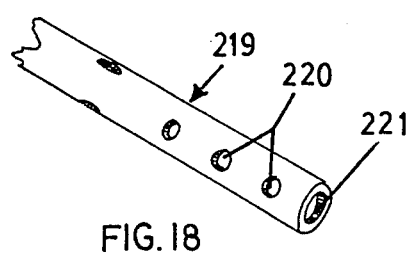
FIG. 16
FIG. 18

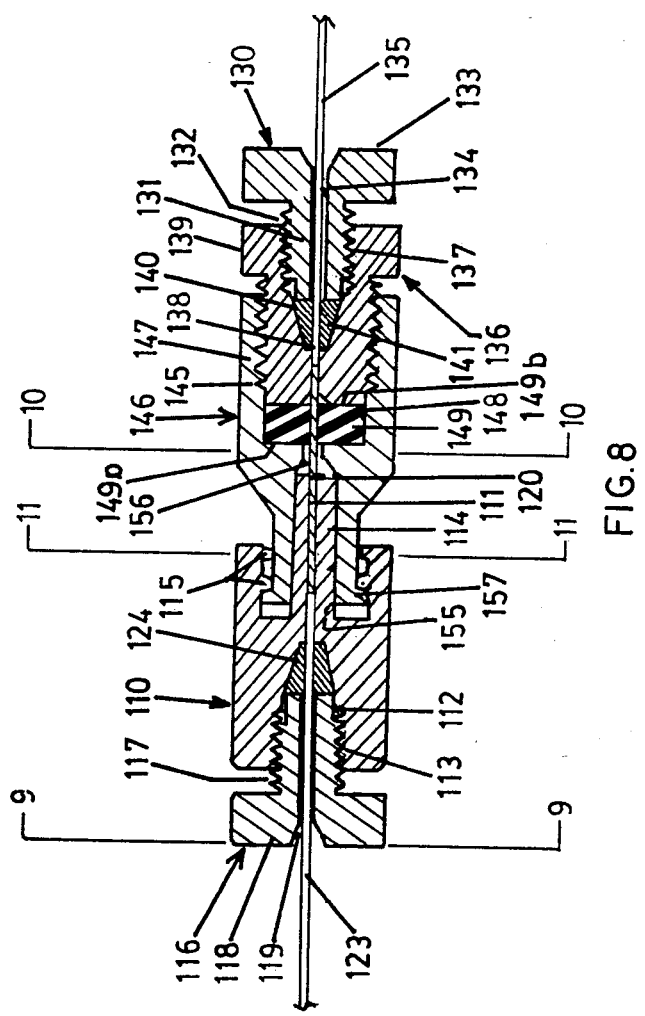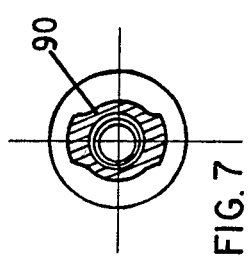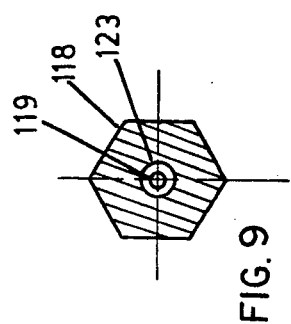

ASSEMBLY WITH SEPTUM FITTING FOR CONNECTING ADAPTOR AND FLUID TUBE

BACKGROUND OF THE INVENTION

This invention relates to an assembly that connects an adaptor and needle to a tube for fluids, such as a catheter, feed line for chemicals, etc.

In medical applications it is often required to disconnect a drug delivery system connected to a catheter such as for changing reservoirs or moving the patient. The assembly of this invention, including a septum fitting, permits the disconnection and reconnection of a drug delivery system to an inserted catheter line while still maintaining sterility and leak proof characteristics within the catheter.

Moreover, outpatient treatment for various illnesses frequently necessitates repeated injections of drugs. In order to reduce the costs of the equipment used for these multiple injections, it would be preferable to employ an injection system that can be reused rather than being discarded after a single use. The injection system must provide sterility, leak proof properties and freedom from particulate contamination.

Also, a problem is posed arising from memory effects in lines used for drug or chemical delivery; hence, a change from one drug or chemical to another may cause undesirable effects. A low dead volume fitting would reduce these memory effects and minimize the loss of expensive drugs or chemicals.

Finally, an injection system should be provided having components that are inexpensive and readily manufactured, and/or which can be purchased as off-the-shelf items.

THE INVENTION

According to the invention, there is provided an assembly for connecting a needle and associated system to an outlet fluid tube, such as a catheter, etc. A septum is positioned within the assembly between the outlet fluid tube (e.g. a catheter) and the inserted needle with its adaptor holder. When the needle and adaptor are mounted within the assembly, their size and shape align the needle so that it can pierce the central portion of the cavity, and thereby align with the bore of the outlet tube as it enters the septum. Use of the septum enables a leak proof and sterile connection to be made between the inlet of the assembly and the outlet fluid tube.

Upon completion of a fluid injection through the needle and outlet tube, the needle can be withdrawn from the septum which then reseals and maintains a sterile and leak proof seal between the inlet and outlet to the assembly. Hence, use of the septum enables the assembly to be reused, rather than necessitating being discarded after a single injection and permits several drug reservoir changes while maintaining internal sterility of the in-dwelling catheter.

If desired, the inlet walls of the assembly may be tapered to conform with corresponding sidewalls of the adaptor to provide additional leak proof sealing and sterile properties. This taper also serves as a stop for the needle when it is being inserted through the septum.

For applications where a quick disconnect, low pressure tube union is desired, a septum fitting may be formed to accept a ferrule and nut assembly. A tube may then be connected to the fitting housing by tightening the ferrule fitting. Use of a ferrule enables the septum to be employed in a high precision, low dead volume fitting.

Additionally, when tubing is connected to the fitting by direct bonding (such as with a soft catheter), or connected with a ferrule and nut, the cavity between the septum and the outlet tube can be configured to provide a minimum volume, and thus reduce the dead space within the fitting.

BRIEF DESCRIPTION OF THE DRAWINGS

FIG. 5 is a cross sectional view in side elevation of the assembly showing a stylet inserted through the assembly, septum and catheter;

FIG. 7 is a transverse cross sectional view taken along lines 7—7 of FIG. 6;

FIG. 8 is a cross sectional view in side elevation of an assembly providing a quick disconnect, low dead volume union useful in the field of analytical chemistry;

FIGS. 9, 10 and 11 are transverse sectional views of FIG. 8 taken along lines 9—9, 10—10, and 11—11 of FIG. 8;

FIG. 14 is a cross sectional view in side elevation showing the assembly of this invention with a luer lock end cap closure, at the proximal end;

FIG. 15 is a cross sectional view in side elevation showing one type of end perforated catheter useful in the assembly of this invention;

FIG. 16 is a cross sectional view in side elevation showing a catheter end with side slits, suitable for use in this invention;

FIG. 17 is an external perspective view of a slit catheter similar to FIG. 16, with an open end hole; and, FIG. 18 is an external perspective view of the catheter shown in FIG. 15, with an open end hole.

DESCRIPTION OF THE PREFERRED EMBODIMENTS

Figure 1:
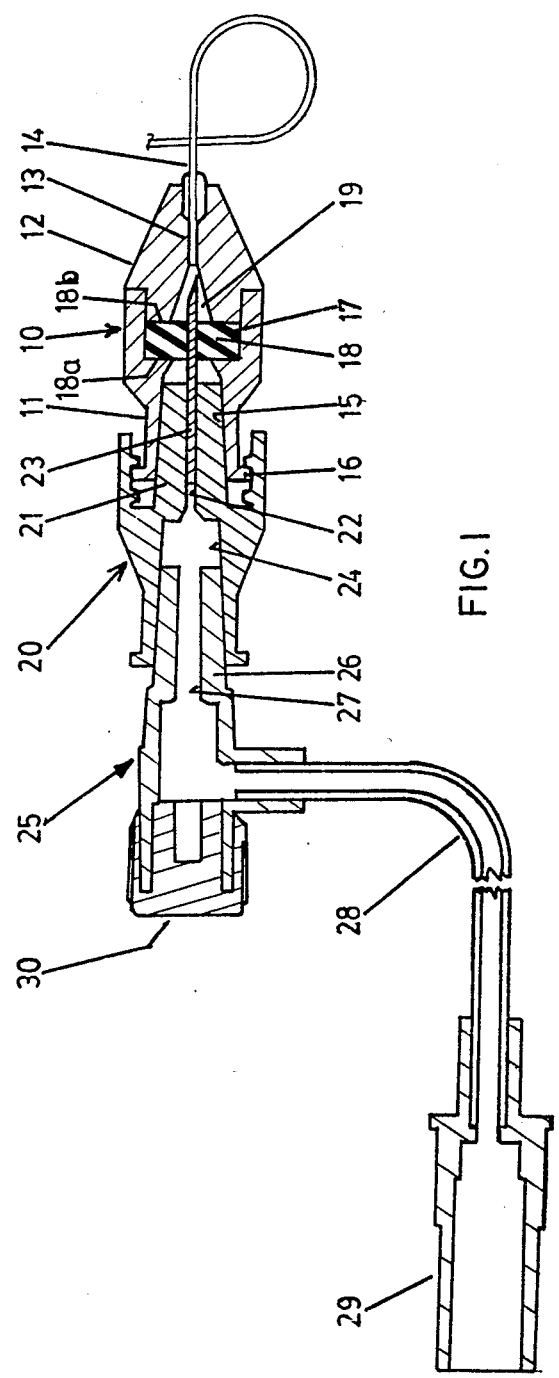
FIG. 1 is a cross sectional view in side elevation showing the assembly device of the invention including the septum, needle, adaptor fitting, and standard luer extension set.

The assembly 10 of this invention, shown in FIG. 1, includes a proximal component 11, and distal component 12 connected thereto. The two components may be connected by press fitting, threading, snap connections, bonding, etc. The distal component 12 defines a central bore 13, and a catheter 14 is mounted, e.g. by bonding therein. The proximal component 11 provides a central bore 15 that is inwardly tapered to receive an adaptor fitting, and the end of the proximal component provides a thread element 16 to enable a quick disconnect from the fitting. A space 17 is defined between the proximal and distal components 11 and 12, and a resealable, sterile septum 18 of desired material is fitted into the space 17. When assembled, the distal and proximal components 12, 11 seal against both faces 18b, 18a, respectively of the septum 18. Thus, the proximal component 11 forms a seal with surface 18a, and the distal component forms a seal with surface 18b. A cavity 19 is defined between the septum and central bore 13 of the proximal component 11. An adaptor fitting 20 at its forward end provides a tapered male connector 21 that fits into the corresponding tapered central bore 15 of the proximal component. The male connector 21 defines a central bore 22 that mounts a hypodermic needle 23. At its rearward end, the fitting defines an inwardly tapered bore 24 for receiving a standard luer extension "T" 25. A tapered male connector 26 defining a hollow bore 27 is inserted into the bore 24 of the adaptor fitting 20. A tube 28 is connected via the extension "T" 25 to the adaptor fitting 20. This enables a connection between a large tube 28, and a small tube 14, i.e., the catheter. Tube 28 may be connected by an extension 29 to an I.V. source, drug reservoir, etc. If desired, additional medication may be fed through the extension end 30.

When assembled, the adaptor fitting 20 with the hypodermic needle 23 is inserted into the central bore 15 of the proximal component 11, and the needle extends through the septum 18 so that the tip of the needle projects into the space 19. If desired, the space 19 can be shaped to minimize the 'dead space' between the needle tip and the central bore 13 of the distal component 13. The septum forms a seal around the needle and maintains the internal volume, including that of space 19, sterile and free from contamination by particulate matter and bacteria. The tapering side walls of the male connector 21 mate with the corresponding tapered bore 15 to provide additional sealing. Also, the tapering contact enables the needle to be centered as the male connector 21 moves along the bore. The male connector 26 of the extension "T" is then inserted into the bore 24 of the adaptor fitting 20, and the system is now ready for use.

Upon completion of injecting a particular drug, medication etc., the extension "T" may be removed, and a new drug reservoir or medication unit is attached. When the adaptor fitting 20 is removed with the extension "T" set, the septum will self seal thereby maintaining the internal volume, including space 19 sterile and free from contamination, as before. Thus space 19 will be maintained in a sterile condition with respect to the catheter 14, and free from say, pathogens, dust particles, smoke, undesirable fumes, and other sources of contamination, etc. The assembly 10 may therefore be reused at considerable cost saving, and increased comfort to the patient because a new catheter need not be inserted.

Figure 3:
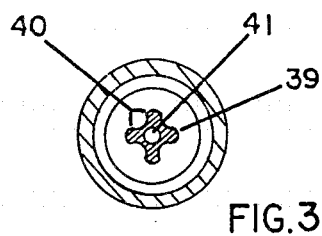
FIGS. 3 and 4 are end views of the syringe and distal portion of the assembly, taken along the lines 3—3, and 4—4, respectively of FIG. 2.
Figure 4:
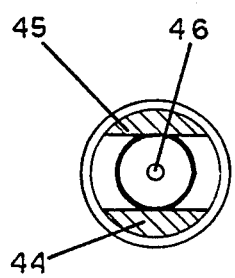
Figure 2:
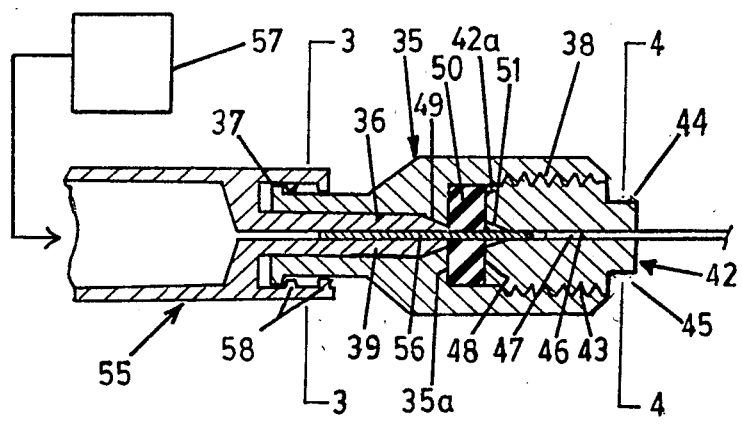
FIG. 2 is a cross sectional view in side elevation of a syringe barrel and needle mounted within the assembly device, and providing a low, dead volume space between the needle and catheter.

Another embodiment of the assembly of this invention is shown in FIGS. 2-4, and is manufactured of metal such as stainless steel, rather than of molded plastic, as in FIG. 1. The proximal component 35 defines a central bore 36, a rear, external locking thread 37, and is internally threaded 38 at the front end.

The distal component 42 provides external threads 43 that engage the threads 38 of the proximal component 35. The end portion of the distal component is milled to form flatterned portions 44, 45 to fit a wrench for tightening purposes. A bore 46 is defined centrally of the distal component into which a catheter 47 is fitted or bonded. A space 48 is defined between the proximal component 35 and the distal component 42, and a septum 50 is fitted into the space 48. When the distal component 42 is tightened into the proximal component 35, both faces of the septum 50 form a seal with the engaging component. The proximal component 35 forms a seal with surface 35a, and the distal component 42 forms a seal with surface 42a. The distal component is configured to provide a minimum dead space 51 between the septum and the entry to the catheter bore 46. This reduces or minimizes the amount of drug solution that is lost in the system, and reduces the 'memory' effects when switching from one drug regime to another.

A syringe barrel 55 and hypodermic needle 56 are adapted for insertion into the bore of the proximal component 35. If desired, an infusion pump 57 may be connected to the syringe barrel 55. A guide portion 39 having flutes 40 and a central bore 41 is molded as part of the syringe barrel 55. The hypodermic needle 56 is bonded into the bore 41. When the needle and guide portion 56, 39 are inserted into the bore 36, the flutes 40 will guide the needle placement through the septum 50 so that the needle end aligns with the bore 46. The forward barrel portion of the syringe has quick disconnect threads 58 to engage threads 37 of the proximal component. A positive stop is provided by engagement of the flutes 40 with the end taper 49 of bore 36. The distal component 42 may be removed allowing replacement of the septum 50 and cleaning of the components 35 and 42.

Another embodiment of this invention is shown in FIG. 5, and employs a stylet for insertion through the septum into a very small size (e.g. 28 gauge) catheter to impart stiffness thereto. The catheter and stylet are inserted into a break-away needle, and following insertion of the needle into a vein, artery, or the like, the stiffened catheter and stylet are both fed through the needle into the vein. The needle is then withdrawn from the puncture site and split away from the catheter, and the stylet is withdrawn from the catheter.

The proximal end 60 and distal end 61 of the assembly in FIG. 5 are both manufactured of plastic and define a space 62 between them into which is placed the sterile septum 63. The catheter 64 is bonded into the bore 65 of the distal end 61. A male stylet 68 is attached to the stylet holder 66; the stylet projects through the septum 63 and into the catheter to the tip. After the catheter has been inserted into a vein, the holder 66 and stylet 68 are removed. The proximal end 60 may be provided with an external end thread 69 so that the bore 67 can be capped and thereby reduce exposure of the septum to non-sterile conditions following removal of the male stylet holder 66.

Figure 6:
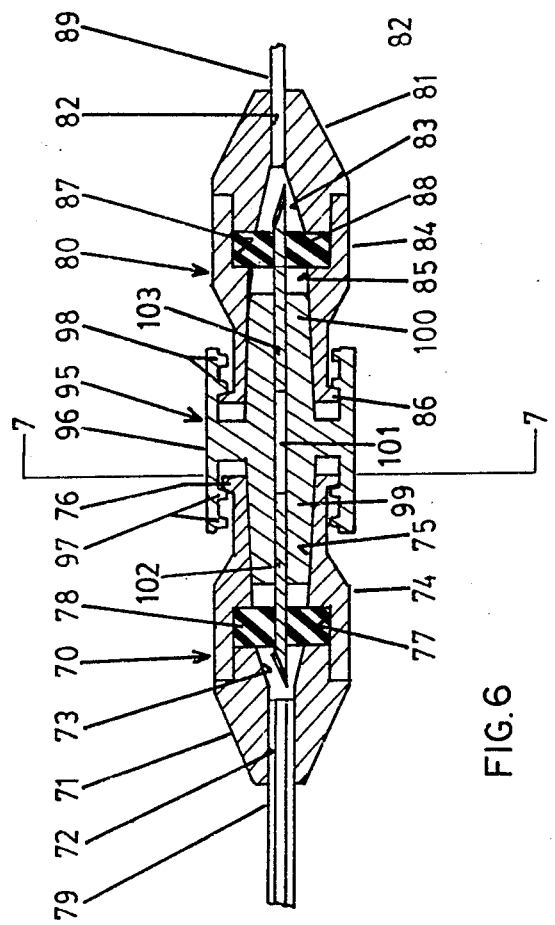
FIG. 6 is a cross sectional view in side elevation showing a dual adaptor connecting two septum fittings bonded to tubes of different diameters.

In FIG. 6, another embodiment of the invention is shown for connecting a large bore feed line, such as an I.V. drip line, to a smaller feed line such as a catheter. Each side of the connector employs an assembly of the invention. The inlet assembly 70 includes a distal component 71 having an inlet bore 72 with a tapered space 73, and a proximal component 74 attached to the distal component 71. The proximal component 74 defines an inlet bore 75, and an external thread 76 for engaging a union fitting. A space 77 is defined between the proximal and distal components 74, 71, and a septum 78 is sealed between them. A tube 79 is bonded or tightly fitted into the bore 72. The outlet assembly 80 may be of similar construction as assembly 70, and comprises a distal component 81 with an outlet bore 82 having a tapered space 83, and a proximal component 84 attached to the distal component 81. The proximal component 84 has an inlet bore 85, and an external thread 86 to engage a union fitting. A space 87 is defined between the proximal and distal components 84, 81, and a septum 88 seals these two components. A tube 89 is bonded or tightly fitted into the outlet bore 82. FIG. 7 shows an end view of the proximal component 74, with face 90 being shown along section 7—7 of FIG. 6, without the adaptor fitting as inserted.

An adaptor fitting 95 functions to join the inlet assembly 70 and outlet assembly 80. The fitting 95 includes a housing 96 that provides two identical sets of internal threads 97, 98 for engaging corresponding luer lock threads 76 and 86 of the inlet and outlet assemblies. Dual male components 99, 100 are inserted into the matching tapered bores 75, 85 respectively of the proximal components 74, 84. A central bore 101 in axial alignment with bores 72 and 82 is located centrally along male components 99, 100. Needles 102, 103 are bonded or fitted within the bore 101 and project through corresponding septums 78, 88 and into the respective spaces 73, 83 of the distal components 71, 81. If desired, the needles 102, 103 could be formed of a single needle having twin, septum-piercing ends. The arrangement shown in FIG. 6 is useful when a patient is being administered an I.V. injection at a certain rate, and it is desired to perform X-ray or other tests. The adaptor fitting 95 is disconnected from the inlet and outlet ends 70 and 80. This permits the inlet end 70 to remain with the I.V. unit and the outlet end 80 to remain with the patient. It will be appreciated that the septum 78 will provide a leak proof and sterile seal between the inlet end and the I.V. fluid reservoir during the disconnect period. Consequently, an on-off valve is not required. When the patient is reconnected to a new sterile adaptor fitting, the same fluid flow rate from the I.V. reservoir will still prevail, with no additional adjustments in flow or changes in I.V. sets being required. The embodiment shown in FIG. 6 is useful in joining a large diameter tube to a small diameter tube.

Figure 10:
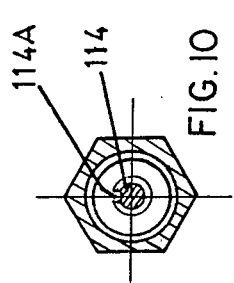

FIG. 8 is an embodiment of a quick disconnect assembly for joining small diameter tubes. The entry coupling 110 provides a central bore 111 that is enlarged 112 and internally threaded 113. The forward end of the entry coupling defines a male guide 114 (FIG. 10), through which the central bore 111 extends; the guide is notched 114a to permit the escape of air during assembly. Quick attach-disconnect threads 115 are provided at the forward end of the coupling. A compression nut 116 is threadably engaged by threads 117 with the internal threads 113 of the entry coupling. The tail end 118 of the compression nut is hexagonally shaped (FIG. 9) to fit a tightening wrench. The compression nut defines a central bore 119 that is aligned with the central bore 111 of the entry coupling. A hypodermic or similar tubing 120 is mounted and bonded within the forward end of bore 111. A feed line 123 is inserted through the bore 119 and passes through a ferrule 124. When the compression nut 116 is threaded into the enlarged bore 112 of the entry coupling 110, it compresses and secures feed line 123 within the ferrule 124 and within the bores 111 and 119 and abutting the needle 120. In certain cases, the needle 120 can be removed and feed line 123 (now sharpened) is passed through bore 111 and abutting tube 135. The ferrule can be made of teflon, polyimide, graphite, metal, etc.

Figure 11:
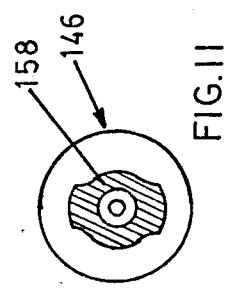

An outlet coupling 130 is provided for connecting an outlet line to the needle 120 with a minimum of dead space. The outlet coupling includes a proximal portion, a septum, a compression insert, a ferrule, and an outlet nut. The outlet nut 131 includes an internal male compression portion that is externally threaded 132, and having an hexagonally shaped end portion 133 to facilitate tightening by a wrench. The nut 131 has an interior bore 134 through which passes an outlet line such as a catheter 135. The outlet nut 131 is threadably connected to a compression insert 136 along internal threads 137. The compression insert 136 defines a bore 138 that is aligned with the bore 134 of the outlet nut 131. The tail end 139 of the compression insert 136 is also hexagonally shaped to facilitate unlocking with a wrench. A ferrule 140 (having the same function as ferrule 124) is inserted into the space 141 between the outlet and pressure couplings, and the catheter 135 is inserted through bores 138, 134 and secured within the ferrule. The outer periphery of the pressure coupling 136 is threaded 145, and threadably engages a proximal portion 146 along its threaded bore 147. A space 148 is defined between the proximal portion 146 and insert 136, and a septum 149 is positioned in the space 148. When the compression insert 136 is tightened into the proximal portion 146, a seal is produced on septum faces 149a and 149b. The proximal portion 146 provides an elongate cavity 155 that engages the male guide 114 of the entry coupling 110, and a central bore 156 connects the cavity 155 and space 148. The forward end of the proximal portion provides a locking thread 157 that makes a quick attach-disconnect with the threads 115 of the coupling 110. FIG. 11 is an end view of outlet coupling 130 disengaged from inlet coupling 110, and indicated as section 11—11 of FIG. 8, and showing the raised face 158. When assembled the bores 119, 111, 156, 138 and 134 are colinear. The ends of the feed line 123, needle 120 and catheter 135 are in close proximity to each other to minimize dead volume space between them. In the configuration of FIG. 8, the septum 149 may be replaced without changing ferrules 124 or 140. Alignment will be still maintained along line 123, needle 120, and line 135 when reconnecting couplings 146 and 110.

Figure 12:
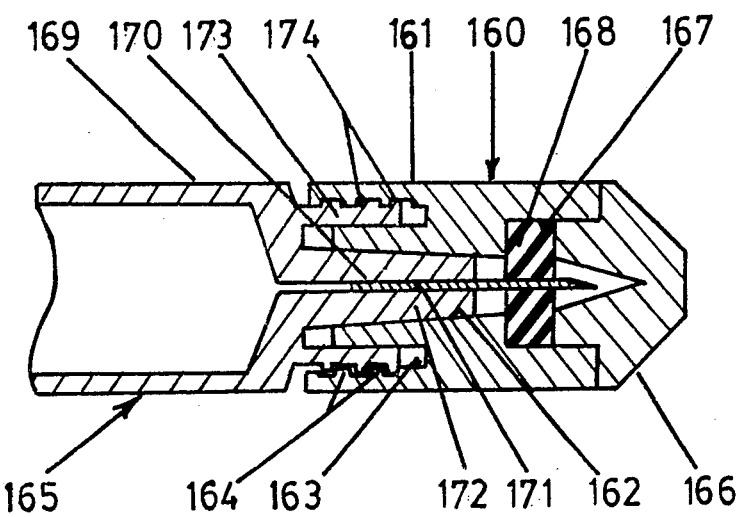
FIG. 12 is a cross sectional view of an assembly of this invention providing an endcap and needle adaptor as part of a syringe barrel.

FIG. 12 illustrates an embodiment of the connector employing a sealing end cap to permit withdrawal of a syringe and needle from a catheter while the latter remains in place in the patient. The syringe can then be reconnected and reused repeatedly, with considerable cost saving.

The connector 160 includes an inlet or proximal portion 161 having a tapered, central inlet bore 162 and a connection slot 163 which is threaded 164 to engage a syringe and needle device 165. A sealing end cap 166 is attached to the proximal portion by threading, a snap on fit, etc. A space 167 is defined between the proximal portion 161 and the end cap 166, and a septum 168 is sealed within the space. The syringe and needle device 165 includes a syringe barrel 169 and connecting needle 170, the latter being centrally located within the bore 171 of a tapered male connector 172. The forward cylindrical end 173 of the syringe provides exterior threads 174 that engages the corresponding threads 164 of the proximal portion 161 to produce a half turn lock. When assembled, the tapered male connector 172 mates with the corresponding tapered inlet bore 162, and the needle 170 pierces the septum 168. Together with the septum and tapering fits of the connector 172 and inlet bore 162, a good sterile seal is provided between the needle and external environment. When it is desired to reuse the device or use it for the first time, the connector 160 is replaced by an assembly, as previously described, with an attached catheter. Following use of the needle-catheter connector, the septum assembly and attached catheter is disconnected from the syringe barrel 165 and replaced by the connector 160.

Figure 13:
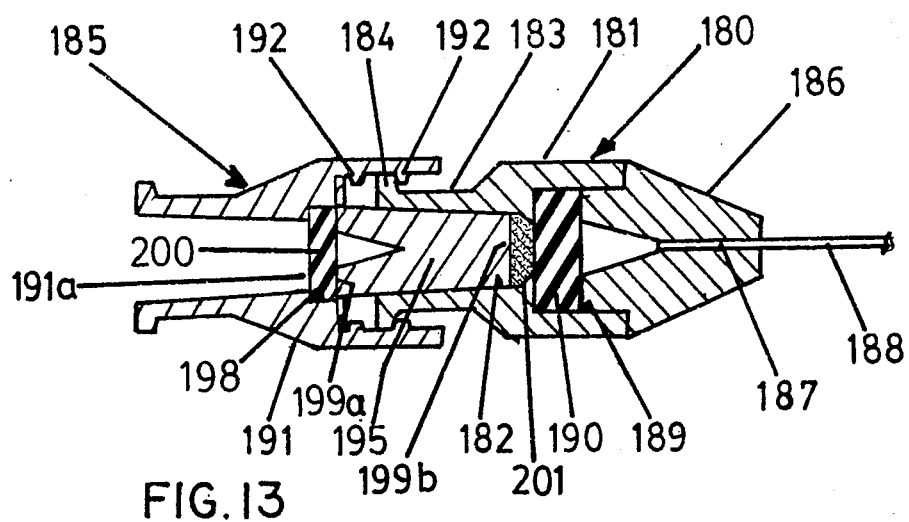
FIG. 13 is a cross sectional view in side elevation of an assembly of this invention having end caps at both ends of the assembly.

The assembly of FIG. 13 provides a double end cap arrangement. This type of fitting may be used to end cap the previously described septum type of fitting or to cap any adjoining reservoir or adaptor fitting with an attached needle. The embodiment shown in FIG. 13 is designed to seal the connector 180 when the needle is removed; the catheter remains in place in the patient along with the attached, sealed connector. This is useful when a new or different syringe and needle is required for injection of a different drug or medication. The proximal portion 181 of the connector 180 defines a tapered central bore 182 and a connection sleeve 183 that is threaded 184 to engage a compression portion 185 for a syringe and needle. The distal portion 186 of the connector is connected to the proximal portion 181, and provides a central bore 187 to which is bonded or press fitted a catheter 188. A space 189 is created between the proximal portion 181 and distal portion 186, and a septum 190 is positioned in this space. The compression portion 185 provides a cylindrical insertion sleeve 191 that is threaded 192 to engage the threads 184 of the connection sleeve 183. The compression portion 185 is bonded to a forward, tapered, sealing male compression insert 195 that moves along and fits into the tapered bore 182. A space is formed between the back end 199a of the compression insert 195, and the compression portion 185, and a septum 200 is sealed in the space 198 by faces 199a and 191a. The compression portion 185 with the septum serve as a needle end cap, as described in FIG. 12. A sterilizing swab 201 is bonded to the front 199b of the male compression insert 195. The swab 201 contacts the exposed surface of septum 190 when the fitting 185 is connected to assembly 180.

When a syringe and needle are retracted from the central bore 182, they are replaced by the compression portion 185, and compression insert 195. Together with the sterilizing swab 201, this will protect the entry side of the septum 190 against bacteria, dust particels, foreign matter, etc., during the period when the syringe and needle are not in use. Maintaining a sterile entrance surface on the septum will prevent entrainment of contaminants upon reinsertion of the needle.

The assembly in FIG. 14, includes an end cap 202 for covering the open bore 203 of the assembly 204 when the stylet holder and stylet, or syringe and needle are removed. A sterilizing swab 205 is inserted into the bore 203 and abutting the septum 206 to reduce direct contact of the septum with ambient air and minimize septum contamination. Hence, the possibility of contamination of space 207 will be minimized when inserting a needle adaptor through the septum.

FIGS. 15-18 illustrate various embodiments of a perforated or slit catheter that may be used to increase the drug or chemical infusion area in the proximal or indwelling portion of the catheter. These slits, folds and perforations minimize the risk of clogging from aggregation or occlusion, and permit drug delivery over a larger tissue area. In FIG. 15, the catheter 210 is perforated 211 and end sealed 212, while in FIG. 16, the catheter 213 is provided with slits 214, and is also end sealed 215. In FIG. 17, the catheter 216 is open at the end 217 and has one or more slits 218 to prevent reflux of fluid or blocking with tissue or capillary walls if positive pressure inside the catheter (i.e. the outflow) decreases. FIG. 18, is a view similar to FIG. 15, but in perspective, showing a catheter 219 having perforations 220 and an open end 221.

We claim:

1. An assembly, including a septum fitting for a tube end, and comprising:
   a. a distal end cap defining a central bore therethrough, and an enlarged bore entry;
   b. a proximal connector connected with the distal end cap, a space being defined between the end cap and the proximal connector;
   c. an external adaptor fitting having a septum piercing tube for fluid flow therethrough, a space being defined between the end cap and the proximal connector; and,
   d. a septum disposed within the said space and adapted for compression between the proximal connector and distal end cap, the septum providing a self-sealing sterile, static barrier to a fluid being fed from the adaptor fitting through the septum piercing tube and the proximal connector, and then through the septum and into the bore entry;
whereby, when the assembly is disconnected from the external adaptor, and the tube is removed, the septum maintains a self-sealing, sterile barrier to the bore entry and bore, and when the assembly is connected to the adaptor fitting, fluid flow may be resumed while maintaining the sterile, static seal peripherally of the septum and circumferentially along the tube.

2. The assembly of claim 1, providing a minimum dead space between the septum and entry to the bore.

3. The assembly of claim 1, prividing mating and locking means between the external adaptor and the proximal connector.

4. The assembly of claim 3, in which the external adaptor provides a male connector for interfitting and taper sealing, and including a threaded lock between the adaptor and connector.

5. The assembly of claim 1, in which the septum piercing tube is a needle.

6. The assembly of claim 1, in which the distal end cap, proximal connector and external adaptor are disconnectably all joined together.

7. The assembly of claim 1, in which an outlet tube is bonded to the bore of the distal end cap.

8. The assembly of 7, 8, in which the outlet tube is bonded with a ferrule to the said bore.

9. The assembly of claim 1, in which the external adaptor includes a syringe barrel.

10. The assembly of claim 1, in which the said needle is mounted into the adaptor fitting.

11. The assembly of claim 1, in which the adaptor fitting includes a luer lock.

12. The assembly of claim 1, in which the adaptor fitting comprises a housing which joins two septum fittings.

13. The assembly of claim 1, including an infusion pump.

14. The assembly of claim 1, in which the proximal and distal components are permanently connected, and the external adaptor is disconnectably attached thereto.

15. The assembly of claim 1, including an end cap for the adaptor fitting.

16. The assembly of claim 1, including an end cap for the proximal connector.

17. The assembly of claim 1, including a slit catheter mounted within the central bore of the distal end cap.

18. The assembly of claim 1, including a perforated catheter mounted within the central bore of the distal end cap.

19. A method of effecting a sterile seal for movement of fluid from a fluid source through an outlet tube when the fluid movement is discontinued, comprising:

a. providing an assembly having a distal end cap defining an enlarged bore entry, a central bore therethrough, and an outlet tube mounted within the central bore;

b. providing a proximal connector connected with the distal end cap, a space being defined between the end cap and the proximal connector;

c. providing an external adaptor fitting having a septum piercing tube for fluid flow therethrough, a space being defined between the end cap and the proximal connector; and, d. disposing a septum within the said space and adapted for compression between the proximal connector and distal end cap;

e. feeding a fluid through the assembly and out the outlet tube, the septum providing a self-sealing sterile static barrier to the said fluid as it is fed from the adaptor fitting through the septum piercing tube, the proximal connector, the septum, the distal end cap, and the outlet tube; whereby, when the assembly is disconnected from the external adaptor, and the tube is removed, the septum maintains a self-sealing, sterile barrier to the bore entry and bore, and when the assembly is connected to the adaptor fitting, fluid flow may be resumed while maintaining the sterile, static seal peripherally of the septum and circumferentially along the tube.

* * * * *